US010478388B2

(12) United States Patent
Wang et al.

(10) Patent No.: US 10,478,388 B2
(45) Date of Patent: Nov. 19, 2019

(54) SKIN ENGAGING SHAVING AID MEMBER COMPRISING AT LEAST ONE THERMALLY RESILIENT SENSATE

(71) Applicant: The Gillette Company, Boston, MA (US)

(72) Inventors: Xiandong Wang, Acton, MA (US); Fatima Abdulhussain Jabalpurwala, Waltham, MA (US); Katharine Anne Bakes, Cincinnati, OH (US)

(73) Assignee: The Gillette Company LLC, Boston, MA (US)

( * ) Notice: Subject to any disclaimer, the term of this patent is extended or adjusted under 35 U.S.C. 154(b) by 343 days.

(21) Appl. No.: 14/036,439

(22) Filed: Sep. 25, 2013

(65) Prior Publication Data

US 2014/0090254 A1    Apr. 3, 2014

(30) Foreign Application Priority Data

Sep. 28, 2012   (EP) .................................. 61/707013

(51) Int. Cl.
| | |
|---|---|
| *A61K 8/42* | (2006.01) |
| *A61K 8/81* | (2006.01) |
| *B29C 45/00* | (2006.01) |
| *B26B 21/44* | (2006.01) |
| *A61Q 9/02* | (2006.01) |

(52) U.S. Cl.
CPC .............. *A61K 8/42* (2013.01); *A61K 8/8117* (2013.01); *A61Q 9/02* (2013.01); *B26B 21/44* (2013.01); *B26B 21/443* (2013.01); *B29C 45/00* (2013.01); *A61K 2800/244* (2013.01); *A61K 2800/87* (2013.01)

(58) Field of Classification Search
CPC .. A61K 8/42; A61K 8/8117; A61K 2800/244; A61K 2800/87; B29C 45/00; B26B 21/443; B26B 21/44; A61Q 9/02
See application file for complete search history.

(56) References Cited

U.S. PATENT DOCUMENTS

| | | | |
|---|---|---|---|
| 5,095,619 | A | 3/1992 | Davis et al. |
| 5,134,775 | A | 8/1992 | Althaus et al. |
| 5,451,404 | A | 9/1995 | Furman |
| 5,653,971 | A | 8/1997 | Badin et al. |
| 5,711,076 | A | 1/1998 | Yin et al. |
| 5,713,131 | A | 2/1998 | Rogers et al. |
| 6,295,733 | B1 | 10/2001 | Wexler et al. |
| 6,298,558 | B1 | 10/2001 | Tseng et al. |

(Continued)

FOREIGN PATENT DOCUMENTS

| | | |
|---|---|---|
| WO | WO 2012/116466 | 9/2012 |
| WO | WO 2014/052389 | 4/2014 |
| WO | WO 2014/052390 | 4/2014 |

OTHER PUBLICATIONS

John C. Leffingwell: "Cool without Menthol & Cooler than Menthol and Cooling Compounds as Insect Repellents", Internet Citation, Apr. 10, 2010, pp. 1-19. URL:http://web.archive.org/web/20101203145738/http://leffingwell.com/cooler_than_menthol.htm.

*Primary Examiner* — Rachael E Bredefeld
(74) *Attorney, Agent, or Firm* — Ronald Terk Sia; Kevin C. Johnson

(57) ABSTRACT

A skin engaging shaving aid member suitable for use in a shaving device, said skin engaging shaving aid member comprising a thermally resilient sensate such as N-substituted menthanecarboxamide.

9 Claims, 1 Drawing Sheet

(56) References Cited

U.S. PATENT DOCUMENTS

| | | |
|---|---|---|
| 6,301,785 B1 | 10/2001 | Kwiecien et al. |
| 6,944,952 B1 | 9/2005 | Tseng |
| 7,121,754 B2 | 10/2006 | Bressler et al. |
| 7,414,152 B2 | 8/2008 | Galopin et al. |
| 7,482,373 B2 | 1/2009 | Wang et al. |
| 7,662,576 B2 | 2/2010 | Gravina et al. |
| 8,157,918 B2 | 4/2012 | Becker et al. |
| 8,343,465 B2 | 1/2013 | Kolbe et al. |
| 9,119,796 B2 | 9/2015 | Cook et al. |
| 2006/0225285 A1 | 10/2006 | Slavtcheff et al. |
| 2006/0276667 A1* | 12/2006 | Galopin .................. A61K 8/42 558/410 |
| 2007/0077331 A1 | 4/2007 | Kiefer et al. |
| 2008/0031166 A1 | 2/2008 | Fakuda |
| 2008/0300314 A1 | 12/2008 | Galopin et al. |
| 2009/0223057 A1 | 9/2009 | Coope-Epstein et al. |
| 2009/0258041 A1* | 10/2009 | Mongiat et al. ............. 424/401 |
| 2009/0306152 A1 | 12/2009 | Kolbe et al. |
| 2010/0086498 A1 | 4/2010 | Haught et al. |
| 2011/0081303 A1 | 4/2011 | Oertling et al. |
| 2011/0082204 A1 | 4/2011 | Wei |
| 2014/0090255 A1 | 4/2014 | Wang et al. |
| 2015/0272847 A1 | 10/2015 | Wang et al. |
| 2015/0273711 A1 | 10/2015 | Wang et al. |

\* cited by examiner

SKIN ENGAGING SHAVING AID MEMBER COMPRISING AT LEAST ONE THERMALLY RESILIENT SENSATE

BACKGROUND OF THE INVENTION

The use of shaving aids on razor blades to provide lubrication benefits during the shave is known. See e.g., U.S. Pat. Nos. 7,121,754; 6,298,558; 5,711,076; 5,134,775; 6,301,785 and U.S. Patent Publ. Nos. 2009/0223057, 2006/0225285. The use of certain cooling sensates in shaving aids has also been disclosed. See e.g., U.S. Patent Pubs. 2007/0077331, 2008/031166, 2008/0300314A1; U.S. Pat. Nos. 5,451,404, and 7,482,373; and WO2007/036814A2. For example, it has been described that cooling agents and/or essential oils can be included in the shaving aid to deliver a fresh and cool feel after contact. It has been reported, however, that a substantial amount of the essential oil can be lost due to volatilization prior to use. See U.S. Pat. No. 5,095,619. U.S. Pat. No. 5,713,131 attempts to fix this potential problem by introducing non-volatile cooling agents into the shave aid, such as non-volatile menthol analogs. Examples of other shave aids containing menthol and other actives are disclosed in U.S. Pat. Nos. 5,095,619, 6,298,558, 6,944,952, and 6,295,733. See also, U.S. Pat. No. 5,653,971 (disclosing a shaving aid which includes an improved shaving aid composite (or lubricating strip) which contains an inclusion complex of a skin soothing agent, such as menthol, with a cyclodextrin) and, U.S. Pat. No. 5,713,131 (disclosing a non-volatile cooling agent, such as Cooling Agent 10, WS-3, WS-23, Frescolat ML, Frescolat MGA and Menglytate). It has been reported that these shaving aids deliver cooling agent during use.

Many ingredients that are normally used in skin care, however, are not easy to use in a conventional extruded shaving aid. This is because many shaving aids are extruded through a die or otherwise processed at high temperatures, such as from about 160° C. to about 180° C. Formulating extruded shaving aids with cooling agents is challenging since many of these cooling agents have boiling points below the typical shaving aid extrusion temperature. Furthermore, extrusion subjects the shaving aid compositions to high pressure which can also add to the degradation of the cooling agents. One commonly used cooling agent is L-menthol. The addition of this cooling agent as a neat ingredient in a shaving aid has been described but the cooling affect is believed to be limited by the concentration of L-menthol used and lack of shelf life due to its high volatility. Cooling agents having greater cooling intensity are known but they tend to have even lower evaporating temperatures making them less likely to be suitable for the high temperatures and pressures used in conventional shaving aid extrusion.

Various cooling technologies have also been described in cosmetic and/or oral care formulations. See e.g. U.S. Patent Pub. Nos 2009/0311206 and 2009/0306152, both assigned to Beiersdorf, 2006/0276667, 2010/0086498, 2010/0086498, 2011/0081303, and 2011/0082204. Not all cooling technologies however are suitable for processing in normal shaving aid making conditions. In particular, some cooling technologies are believed to be so volatile that they can be lost during the shaving aid making process or otherwise become less active such that they are not perceivable during use. As such, there is a need for technologies which can survive the skin engaging shaving aid member making process while maintaining sufficient molecular activity to provide meaningful or long lasting cooling benefit.

SUMMARY OF THE INVENTION

One aspect of this invention relates to a skin engaging shaving aid member, i.e. suitable for use with a shaving device, such as a razor or depilatory and scraping tool, said skin engaging shaving aid member comprising a matrix comprising at least one of: a water soluble polymer, an emollient, a soap base, and a mixture thereof; and at least one thermally resilient sensate comprising an N-substituted menthanecarboxamide having the formula (I) below:

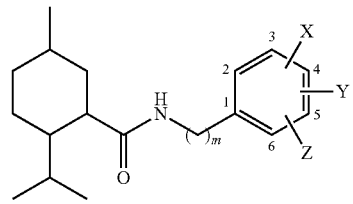

in which m is 0 or 1, Y and Z are selected independently from the group consisting of H, OH, C1-C4 straight or branched alkyl, or, a C1-C4 straight or branched alkoxy, X is (CH2)n-R, where n is 0 or 1 and R is a group with non-bonding electrons, with the provisos that: (a) when Y and Z are H, X is not F, OH, MeO or NO2 in the 4-position and is not OH in the 2 or 6-position (b) when Y or Z is H then X, Y and Z are such that (i) the groups in the 3- and 4-positions are not both OMe, (ii) the groups in the 4- and 5-positions are not both OMe, (iii) the groups in 3- and 5-positions are not OMe if the group in the 4-position is OH, and (iv) the groups in the 3- and 5-positions are not OH if the group in the 4-position is methyl. The thermally resilient sensate can be included at various levels, such as from about 0.01% to about 25%, alternatively from about 1% to about 20%, alternatively from about 5% to about 15%, alternatively from about 7% to 13%, alternatively about 10%. A further aspect of the invention relates to a shaving device comprising the aforementioned skin engaging shaving aid member. Another aspect of the invention relates to a method of making a skin engaging shaving aid member comprising the thermally resilient sensate.

DETAILED DESCRIPTION OF THE INVENTION

I. Thermally Resilient Sensates

Figure 1:
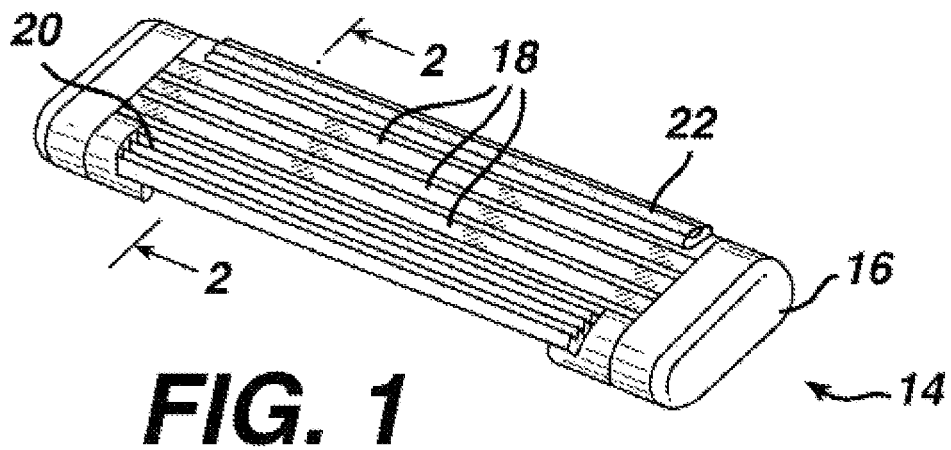
FIG. 1 is a perspective view of a razor cartridge which includes a skin engaging shaving aid member of the present invention.

It is now well established that sensations such as cool or cold can be attributed to activation of receptors at peripheral nerve fibers by a stimulus such as low temperature or a chemical coolant, which produces electrochemical signals that travel to the brain, which then interprets, organizes and integrates the incoming signal(s) into a perception or sensation. Different classes of receptors have been implicated in sensing cold temperatures or chemical coolant stimuli at mammalian sensory nerve fibers. Among these receptors, a major candidate involved in sensing cold has been identified and designated as cold- and menthol-sensitive receptor (CMR1) or TRPM8. The TRPM8 nomenclature for the receptor comes from its characterization as a non-selective cation channel of the transient receptor potential (TRP) family that is activated by stimuli including low temperatures, menthol and other chemical coolants. However, the precise mechanisms underlying the perception of a pleasant cooling sensation on skin or oral surfaces are presently not clearly understood. While it has been demonstrated that the TRPM8 receptor is activated by menthol and other coolants, it is not fully understood what other receptors may be involved and to what extent these receptors need to be stimulated or perhaps suppressed in order that the overall perceived sensation would be pleasant, cooling and refreshing. Sensates have been described in various applications. See e.g. U.S. Patent Publ No. 2010/0086498.

The skin engaging shaving aid member of the present invention comprises at least one thermally resilient sensate. Thermally resilient sensates are defined herein as sensate ingredients which are capable of surviving conventional shaving aid (skin engaging shaving aid member) extrusion conditions but still remain sufficiently active to provide cooling or tingling sensations, typically perceptible by the user, on skin during use in a shaving context. Without intending to be bound by theory, it is believed that the thermally resilient sensate of the present invention can deliver greater cooling intensity even after it is extruded into a skin engaging shaving aid member, compared to sensates that are volatile and can be lost in the making process. In some embodiments, the thermally resilient sensate retains at least 50% of its cooling intensity compared to when it is applied onto skin at the same concentration in a liquid medium, or at least 70%, or at least 90%. Those of skill in the art will understand that skin engaging shaving aid members may also comprise shaving aids and such skin engaging shaving aid members are also commonly referred to as lubricating strips suitable for use on the skin contacting portions of razor cartridges.

Furthermore, the thermally resilient sensates of the present invention provide a greater cooling intensity when provided in a skin engaging shaving aid member beyond the cooling intensity of L-menthol, preferably at least 1.5 times greater cooling intensity, more preferably at least 5 times greater cooling intensity, even more preferably at least about 10 times greater cooling intensity, up to about 20 times greater cooling intensity.

The thermally resilient sensate can be included at a level of from about 0.01% to about 25%, alternatively from about 1% to about 20%, alternatively from about 5% to about 15%, alternatively from about 7% to 13%, alternatively about 10%. Without intending to be bound by theory, it is believed that these levels of thermally resilient sensate provide for an appreciable performance benefit to a meaningful amount of users, particularly at a level of above 5%, and at a level below 15%. It is believe that although some users may find lower levels enjoyable, many may find that there is too low impact. Similarly, although some users may enjoy a higher level above 15%, it may be too much for the majority of intended consumers.

Without intending to be bound by theory, it is believed that the cooling intensities of the thermally resilient sensates are about 10 times the cooling intensity of L-menthol. For example, in U.S. Pat. No. 7,414,152 by Galopin et. al. (Givaudan), N-(4-cyanomethylphenyl)p-menthanecarboxamide (commercially available as FEMA 4496) was about 10× more cooling as compared to menthol at 2 ppm. See Leffingwell, John C. PhD, *Cool without Menthol & Cooler than Menthol and Cooling Compounds as Insect Repellents* (Leffingwell & Associates, Last updated May 4, 2011).

The skin engaging shaving aid member can also optionally comprise an additional coolant.

The thermally resilient sensate comprises an N-substituted menthanecarboxamide, specifically of the Formula (I), below.

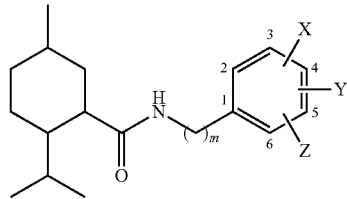

I in which m is 0 or 1, Y and Z are selected independently from the group consisting of H, OH, C1-C4 straight or branched alkyl, or, a C1-C4 straight or branched alkoxy, X is (CH2)n-R, where n is 0 or 1 and R is a group with non-bonding electrons, with the provisos that: (a) when Y and Z are H. X is not F, OH, MeO or NO2 in the 4-position and is not OH in the 2 or 6-position (b) when Y or Z is H then X, Y and Z are such that (i) the groups in the 3- and 4-positions are not both OMe, (ii) the groups in the 4- and 5-positions are not both OMe, (iii) the groups in 3- and 5-positions are not OMe if the group in the 4-position is OH, and (iv) the groups in the 3- and 5-positions are not OH if the group in the 4-position is methyl.

The preferred compounds are those in which X is in the 4-position. The most preferred compounds are when X is in the 4-position and Y and Z are H, OH, Me or OMe.

Preferred groups with non-bonding electrons are halogens, OH, OMe, NO2, CN, Ac, SO2NH2, CHO, CO2H and C1-C4 alkyl carboxylates such as CO2Et.

On specific example of a suitable N-substituted menthanecarboxamide is N-[4-(cyanomethyl)phenyl]-(1R,2S,5R)-2-isopropyl-5-methylcyclohexanecarboxamide of Formula II.

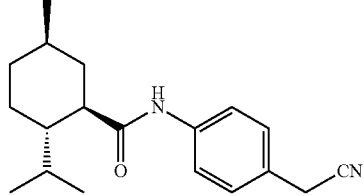

Formula II

This material is also commonly referred to as N-parabenzene acetonitrile menthane carboxamide. See e.g. Research Disclosure RD 522003 (Givaudan), U.S. Patent Pub. Nos 2009/0311206 and 2009/0306152, both assigned to Beiersdorf, 2006/0276667, 2010/0086498, and U.S. Pat. No. 7,414,152. Various methods to manufacture N-parabenzene acetonitrile menthane carboxamide have been disclosed, including in U.S. Patent Publ. 2006/027667, 2008/0300314, 2010/0040563, and 2010/0076080. N-parabenzene acetonitrile menthane carboxamide is commercially available from suppliers under CAS 852379-28-3, which can be supplied as a white powder with an assay of 94% to 100% and a melting point of 145° C. at 760 mm Hg.

In some embodiments, the skin engaging shaving aid member further comprises one or more additional sensates other than the thermally resilient sensates disclosed above. For example, menthol is widely used as a cooling agent, but menthol can also produce other sensations including tingling, burning, prickling and stinging as well as a minty smell and bitter taste. Thus, it can be inferred that menthol acts on many different receptors, including cold, warm, pain and taste receptors. However, it is not readily discernible how to isolate which receptor activities would result in a specific sensation such as pleasant cooling without the undesirable sensations such as bitterness or irritation. Neither is it apparent how to control the activity of coolants or other sensory agents such that only the desired sensation is elicited from use of a particular sensory agent. As such, the present invention is focused on the addition of specific synthetic derivatives of cyclohexane (described above) to act as sensates to deliver cooling benefit to users during the shaving process. Additional sensates can be used to further supplement the cooling feel.

A large number of coolant compounds of natural or synthetic origin are known. The most well-known compound is menthol, particularly l-menthol, which is found naturally in peppermint oil, notably of *Mentha arvensis* L and *Mentha viridis* L. Of the isomers of menthol, the 1-isomer occurs most widely in nature and is typically what is referred by the name menthol having coolant properties. L-menthol has the characteristic peppermint odor, has a clean fresh taste and exerts a cooling sensation when applied to the skin and mucosal surfaces. Other isomers of menthol (neomenthol, isomenthol and neoisomenthol) have somewhat similar, but not identical odor and taste, i.e., some having disagreeable notes described as earthy, camphor, musty. The biggest difference among the isomers is in their cooling potency. L-menthol is reported to provide the most potent cooling, i.e., having the lowest cooling threshold (i.e., the concentration where the cooling effect could be clearly recognized) of about 800 ppb. At this level, there is no cooling effect for the other isomers. For example, d-neomenthol is reported to have a cooling threshold of about 25,000 ppb and l-neomenthol about 3,000 ppb. [R. Emberger and R. Hopp, "Synthesis and Sensory Characterization of Menthol Enantiomers and Their Derivatives for the Use in Nature Identical Peppermint Oils," Specialty Chemicals (1987), 7(3), 193-201]. This study demonstrated the outstanding sensory properties of l-menthol in terms or cooling and freshness and the influence of stereochemistry on the activity of these molecules.

Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series such as WS-5 (N-ethoxycarbonylmethyl-ρ-menthan-3-carboxamide), and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. TK-10 is described in U.S. Pat. No. 4,459,425 to Amano et al. Other alcohol and ether derivatives of menthol are described e.g., in GB 1,315,626 and in U.S. Pat. Nos. 4,029,759; 5,608,119; and 6,956,139. WS-3 and other carboxamide cooling agents are described for example in U.S. Pat. Nos. 4,136,163; 4,150,052; 4,153,679; 4,157,384; 4,178,459 and 4,230,688. Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)$_p$-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide.

Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,111,127; 3,917,613; 3,991,178; 5,5703,123; 5,725,865; 5,843,466; 6,365,215; 6,451,844; and 6,884,903. Ketal derivatives are described, e.g., in U.S. Pat. Nos. 5,266,592; 5,977,166 and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., *J. Pharm. Pharmacol.* (1983), 35:110-112. Reviews on the coolant activity of menthol and synthetic coolants include H. R. Watson, et al. *J. Soc. Cosmet. Chem.* (1978), 29, 185-200 and R. Eccles, *J. Pharm. Pharmacol.*, (1994), 46, 618-630.

Without intending to be bound by theory, it is believed that the present N-substituted menthanecarboxamide triggers both TRPM8 and TRPA1 (Tingle/numb/burn) receptor, while L-menthol triggers TRPM8, TRPA1 and warming receptors TRPV1 & TRPV3. It is believed that the present system comprising the synthetic derivatives of cyclohexane described above, with the optional additional sensates makes it possible to achieve in-shave and long-last cooling benefits.

II. Matrix Material

The skin engaging shaving aid member further comprises a matrix material within which the thermally resilient sensate is present. The matrix material can be in various forms, as well as mixtures/combinations thereof:

a. Solid Polymeric Matrix

In some embodiments, the matrix comprises a water soluble polymer, for example a polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, silicone polymers, and mixtures thereof. In some embodiments, said water soluble polymer is selected from the group consisting of polyethylene oxide, polyethylene glycol, and mixtures thereof.

In some embodiments, the skin engaging shaving aid member comprises any other ingredients commonly found in commercially available skin engaging shaving aid members, such as those used on razor cartridges by Gillette, Schick or BIC. Non-limiting examples of such skin engaging shaving aid members include those disclosed in U.S. Pat. Nos. 6,301,785, 6,442,839, 6,298,558, 6,302,785, and U.S. Patent Pubs 2008/060201, and 2009/0223057. In some embodiments, the skin engaging shaving aid member further comprises a skin engaging shaving aid member ingredient selected from the group consisting of polyethylene oxide, polyvinyl pyrrolidone, polyacrylamide, hydroxypropyl cellulose, polyvinyl imidazoline, polyethylene glycol, poly vinyl alcohol, polyhydroxyethylmethacrylate, silicone copolymers, sucrose stearate, vitamin E, soaps, surfactants, panthenol, aloe, plasticizers, such as polyethylene glycol; beard softeners; additional lubricants, such as silicone oil, Teflon® polytetrafluoroethylene powders (manufactured by DuPont), and waxes; essential oils such as menthol, camphor, eugenol, eucalyptol, safrol and methyl salicylate; tackifiers such as Hercules Regalrez 1094 and 1126; non-volatile cooling agents, inclusion complexes of skin-soothing agents with cyclodextrins; fragrances; antipruritic/counterirritant materials; antimicrobial/keratolytic materials such as Resorcinol; anti-inflammatory agents such as Candilla wax and glycyrrhetinic acid; astringents such as zinc sulfate; surfactants such as pluronic and iconol materials; compatibilizers such as styrene-b-EO copolymers; mineral oil, polycaprolactone (PCL), and combinations thereof.

The water-soluble polymer will preferably comprise at least 50%, more preferably at least 60%, by weight of the skin engaging shaving aid member, up to about 99%, (or up to about 90% of the solid polymeric matrix). The more preferred water soluble polymers are the polyethylene oxides generally known as POLYOX (available from Union Carbide Corporation) or ALKOX (available from Meisei Chemical Works, Kyoto, Japan). These polyethylene oxides will preferably have molecular weights in unified atomic mass units, daltons, or g/mol (mol·wt·s) of about 100,000 to 6 million, most preferably about 300,000 to 5 million. The most preferred polyethylene oxide comprises a blend of about 40% to 80% of polyethylene oxide having an average mol·wt. of about 5 million (e.g. POLYOX COAGULANT) and about 60% to 20% of polyethylene oxide having an average mol·wt. of about 300,000 (e.g. POLYOX WSR-N-750). The polyethylene oxide blend may also advantageously contain up to about 10% by weight of a low mol·wt. (i.e. MW<10,000) polyethylene glycol such as PEG-100.

In some embodiments, the matrix further comprises from about 0.5% to about 50%, preferably from about 1% to about 20%, polycaprolactone (preferably mol·wt. of 30,000 to 60,000 daltons). See U.S. Pat. No. 6,302,785.

The skin engaging shaving aid member may contain other conventional skin engaging shaving aid member ingredients, such as low mol·wt. water-soluble release enhancing agents such as polyethylene glycol (MW<10,000, e.g., 1-10% by weight PEG-100), water-swellable release enhancing agents such as cross-linked polyacrylics (e.g., 2-7% by weight), colorants, antioxidants, preservatives, vitamin E, aloe, cooling agents, essential oils, beard softeners, astringents, medicinal agents, etc. Portions that contain a colorant can be designed to release the colorant (e.g., by leaching or abrasion), and thereby cause the strip to change color during shaving, preferably in response to wear of the colored portion, so as to provide an indication to the user that the skin engaging shaving aid member and/or the razor cartridge has reached the end of its effective life or the end of its optimum performance. A portion may contain, for example, between about 0.1% and about 5.0% (preferably between about 0.5% and 3%) colorant by weight.

The matrix can further comprise a water-insoluble polymer in which the water-soluble polymer is dispersed. Preferably, at a level of from about 0% to about 50%, more preferably about 5% to about 40%, and most preferably about 15% to about 35% by weight of the skin engaging shaving aid member of a water-insoluble polymer. Suitable water-insoluble polymers which can be used include polyethylene (PE), polypropylene, polystyrene (PS), butadiene-styrene copolymer (e.g. medium and high impact polystyrene), polyacetal, acrylonitrile-butadiene-styrene copolymer, ethylene vinyl acetate copolymer, polyurethane, and blends thereof such as polypropylene/polystyrene blend or polystyrene/impact polystyrene blend.

One preferred water-insoluble polymer is polystyrene, preferably a general purpose polystyrene, such as NOVA C2345A, or a high impact polystyrene (i.e. polystyrene-butadiene), such as BASF 495F KG21. The strip or any portion should contain a sufficient quantity of water-insoluble polymer to provide adequate mechanical strength, both during production and use.

b. Emollients

In some embodiments, the matrix material comprises at least one emollient. In some embodiments the emollient is hydrophobic. In certain embodiments, the composition can consist essentially of one or more emollients which could form a fluid at 25° C. Where the emollient is fluid form, the fluid is preferably contained within a skin engaging reservoir as disclosed below. In such embodiments, depending on the viscosity of the composition, varying orifice sizes can be used to control the dispensing of emollient during use.

The emollient is liquid, semi-solid and/or solid at room temp. The emollient may comprise one or more hydrocarbon emollients, a lipid, lipophilic skin care actives, or a mixture thereof. Suitable lipids include fatty acyls such as fatty acids, fatty alcohols, esters, triglycerides, fats, butters, and waxes; glycerolipids; glycerophospholipids; sphingolipids; sterol lipids; prenol lipids; saccharolipids; polyketides; lipophilic skin active agent emollients, and mixtures thereof.

Hydrocarbon emollients include straight chain, branched chain, saturated and unsaturated hydrocarbons and mixtures thereof and they may comprise natural or synthetic hydrocarbon emollients and mixtures thereof. Preferred natural hydrocarbon emollients include petrolatum, mineral oil and mixtures thereof. Preferred synthetic hydrocarbon emollients include branched chain hydrocarbons, such as isohexadecane (such as Arlamol HD™ from Croda) and Polydecene (such as Puresyn 2™ from Exxon Mobil).

Fatty alcohol or fatty acid emollients include saturated and unsaturated higher alcohols, especially $C_{12}$-$C_{30}$ fatty alcohols and fatty acids, especially lauric, myristic, palmitic, stearic, arachidic or behenic. Ester emollients include esters of a $C_{12}$-$C_{30}$ alcohol and mixtures thereof, especially isopropyl myristate, isopropyl isostearate and mixtures thereof. Triglyceride emollients include synthetic or natural triglycerides, especially natural triglycerides derived from sunflower, avocado, olive, castor, coconut, cocoa and mixtures thereof. More preferred are coconut-derived triglycerides, such as the commercially available materials Myritol™ 312 and 318 (Cognis), Estasan™ (Croda) and Miglyol™ (Sasol). Fat and butter emollients include coconut butter, shea butter and mixtures thereof. Wax emollients include paraffin wax, microcrystalline wax, candellila, ozokerite and mixtures thereof. Preferably, the emollient comprises paraffin wax. Advantageously, a hydrophobic phase comprises some wax because waxes may bestow further improved hardness and erodability to the solid moisturising composition. Preferably, the erodible, solid moisturizing composition comprises from about 2% to about 20% and more preferably from about 3% to about 15% wax by weight of the erodible, sold moisturizing composition.

Another class of suitable lipids include lipophilic skin active agent emollients which include oil soluble vitamins, such as vitamin E derivatives, including vitamin E acetate and tocopherol nicotinate; oil-soluble vitamin A derivatives, such as retinyl palmitate, lanolin, ceramides, sterols and sterol esters, salicylic acid, camphor, eucalyptol and essential oils.

In some embodiments, the matrix material comprises at least one emollient and a water insoluble structuring polymer. Examples of such compositions have been described as an erodable, solid moisturizing composition described in copending U.S. patent application Ser. No. 13/026,5556 entitled "HAIR REMOVAL DEVICE COMPRISING ERODABLE MOISTURIZER" and Ser. No. 13/026,575 entitled "HAIR REMOVAL DEVICE COMPRISING AN ERODABLE MOISTURIZER", both to Stephens et al, filed Feb. 18, 2010.

As used herein, the term "solid" when used in relation to the erodable, solid moisturizing composition refers to compositions which are solid at 25° C. As used herein, the term "water-insoluble" when used in relation to the structuring polymer, means "very slightly soluble", according to the United States' Pharmacopeia (USP) definition in 31/NF 26 Vol. 2 General Notices, Page Xvii., or less than "very slightly soluble", which, using the USP definition, means that more than 1000 parts of solvent (water, in this case) are needed to dissolve 1 part of solute (the structuring polymer, in this case) at Standard Temperature and Pressure. As used herein, the term "soluble in" when describing the ability of the water-insoluble structuring polymer to dissolve in the hydrophobic phase means "soluble", according to the United States' Pharmacopeia definition in 31/NF 26 Vol. 2 General Notices, Page Xvii., or at least "soluble", using the USP definition, which means that less than 30 parts of solvent (the hydrophobic phase, in this case) are needed to dissolve 1 part of solute (the structuring polymer, in this case) at the melting point of the water-insoluble structuring polymer.

In some embodiments, the matrix with the emollient is an erodable, solid moisturizing composition having a Chatillon Hardness at 25° C. of about 0.50 kg to about 3.25 kg, preferably about 0.75 kg to about 3.00 kg, more preferably about 1.00 kg to about 2.50 kg, measured according to the protocol provided hereinbelow. It is believed that a skin conditioning composition having such Chatillon hardness provides beneficial rates of wear. The Chatillon Hardness Test is disclosed in U.S. patent application Ser. No. 13/026, 556.

The water-insoluble structuring polymer when comprised within the erodable, solid moisturizing composition may be any water-insoluble structuring polymer which bestows appropriate wear properties to the erodable, solid moisturizing composition and is preferably a water-insoluble structuring polymer which may bestow a Chatillon Hardness in the above-defined ranges to the erodable, solid moisturizing composition. The structuring polymer is water-insoluble to assist miscibility with or solubility in the hydrophobic phase (at the melting point of the water-insoluble structuring polymer), which in turn may ensure a homogenous distribution of hydrophobic phase throughout the polymer and thus more even wear properties. In addition, the water soluble nature of the polymer may improve the durability of the polymer (and therefore also the erodible, solid moisturizing composition) versus more hydrophilic polymers which may solubilise and wash away during shaving processes that employ water, such as wet shaving.

In some embodiments, the erodable, solid moisturizing composition comprises from about 2% to about 50%, preferably from about 3% to about 40%, more preferably about 4% to about 12% of water-insoluble structuring polymer by weight of the erodable, solid moisturizing composition. In some embodiments, the water-insoluble structuring polymer comprises a block copolymer. More advantageously, the block copolymer comprises a di-block copolymer, a tri-block copolymer, a multi-block copolymer, a radial block copolymer, a random block copolymer, or a mixture of these polymers. More advantageously still, the block copolymer comprises a tri-block copolymer.

Where the matrix material comprises the solid polymeric matrix, one or more emollients may also be included in the solid polymeric matrix.

c. Soap Base

The matrix material may comprise a soap base, i.e. at least one soap or interrupted soap, e.g., a poured soap base or an extruded soap base. The basic component of the soap base can be a vegetable oil or tallow, saponified or neutralized to form the base, or can be a synthetic poured soap base. Super-fatted materials containing portions (e.g., greater than about 25 weight percent) of coconut acid or other fatty acids may also be used. In some embodiments, the matrix material includes a base comprising a vegetable oil or a tallow or the like, or a combination of the foregoing materials, which is saponified or neutralized. The saponification or neutralization of the vegetable oil or tallow results in the production of glycerol and salts of fatty acids to form the base. The matrix material can include about 50 wt % to about 100 wt % saponified or neutralized base (e.g., about 75 wt % to about 100 wt % saponified or neutralized base), which may be opaque, translucent, or transparent. Exemplary salts of fatty acids that may be produced include sodium carboxylate salts having up to about 22 carbon atoms.

The soap base can be a synthetic soap base. In certain embodiments, the synthetic soap base includes a glycol (e.g., diproylene glycol, propylene glycol, tripropylene glycol, and/or methylpropane diol glycol), glycerin, fatty acid salts (e.g., sodium stearate and/or potassium stearate), C15-C25 alcohols (e.g., behenyl alcohol, stearyl alcohol, cetyl alcohol, and/or myristic alcohol), steareth (e.g., a steareth 21 such as, for example, BriP-721), stearic acid, microcrystalline wax (e.g., microcrystalline wax SP 16, SP 19, SP 16, SP 18, SP-1674, SP 16W, SP 60W, SP 89, Multiwax 180M, X-145, W-445, and/or W-835), one or more surfactants (e.g., Tegobetaine F-50, Lonzaine®, the Mackam® family of surfactants, the Mirataine® family of surfactants, and sodium lauryl ether sulfate ("SLES") (e.g., 25% active SLES).

The soap base can, in certain embodiments, include from about 0.5% to about 30% glycol (e.g., from about 10% to about 25% glycol or from about 12% to about 15% glycol), from about 10% to about 40% glycerin (e.g., from about 18% to about 34% glycerin or from about 18% to about 24% glycerin), from about 20% to about 40% fatty acid salt (e.g., from about 25% to about 40% fatty acid salts (e.g., stearate) or from about 30% to about 35% fatty acid salt), from about 0.1% to about 10% stearic acid (e.g., from about 2 to about 5% stearic acid), from about 0.5% to about 10% microcrystalline wax (e.g., from about 0.5% to about 5% microcrystalline wax or from about 1% to about 3% microcrystalline wax), from about 1% to about 15% betaine (e.g., from about 2% to about 10% active betaine or from about 4% to about 9% active betaine), and from about 1 to about 20% active SLES (e.g., from about 1% to about 20% active SLES or from about 10% to about 15% active SLES), all based on the weight of the soap base. One exemplary poured soap base prior to addition of the thermally resilient sensate includes the following:

| | |
|---|---|
| Dipropylene glycol | 17.2% |
| Glycerin | 21.4% |
| Sodium stearate | 34.4% |
| Stearic acid (Pristerene ® 4980) | 3.7% |
| Microcrystalline wax SP 89 | 1.2% |
| Tegobetaine F-50 | 7.4% |
| SLES, 25% active | 14.7% |

In some embodiments, a combination of base and synthetic surfactants can be employed.

d. Carrier

In some embodiments, the skin engaging shaving aid member further comprises a carrier wherein the matrix, sensate and any other materials can be contained within the carrier and/or present on the carrier. The carrier can be in the form of a tray upon which the matrix material and encapsulated active are applied, or the carrier can form a retaining structure at least partially containing the matrix and encapsulated material. In some embodiments, the carrier forms a reservoir, for example from which shaving aid is dispensed to the skin with or without direct contact between the carrier and the skin, and such as the sheaths disclosed in U.S. Pat. Nos. 6,298,558 and 7,581,318. Especially where the matrix material comprises a fluid or solid intended to be dissolved during shaving, but applicable generally, the carrier is preferably a sheath having one or more dispensing orifices to control the dispensing of one or more of the materials of the skin engaging member. When referring to the compositional make up of the skin engaging shaving aid member, the weight percentages defined herein are determined based on the other components of the skin engaging shaving aid member disclosed herein but not the carrier, unless otherwise specified.

e. Additional Actives in the Matrix i. Optional Cooling Agents

The matrix material may also comprise a neat non-volatile cooling agent or an inclusion complex of a skin-soothing agent with a cyclodextrin, preferably in amounts up to about 25%, most preferably about 10% to about 20%, by weight of the skin engaging shaving aid member. "Neat" as used herein means that the additional actives are present outside the encapsulates and are dispersed within the remainder of the matrix material. By non-volatile cooling agent is meant an agent which has a physiological cooling effect on the skin and which is appreciably less volatile than menthol. Preferably, the nonvolatile cooling agent will be one which when subjected to thermogravimetric analysis (e.g. using a 951 Thermogravimetric Analyzer from Dupont with a 20° C. temperature rise per minute) will retain at least about 50% of its initial weight at a temperature of 160° C., more preferably at least about 80% of its initial weight at a temperature of 160° C., and most preferably at least about 50% of its initial weight at a temperature of 175° C.

Suitable cooling agents which can be utilized include non-volatile menthol analogs such as menthyl lactate, menthyl ethoxyacetate, menthone glycerinacetal, 3-1-menthoxypropane-1,2-diol, ethyl 1-menthyl carbonate, (1S,3S,4R)-ρ-menth-8-en-3-ol, menthyl pyrrolidone 25 carboxylate, N-substituted-ρ-menthane-3-carboxamides (as described in U.S. Pat. No. 4,136,163, which is incorporated herein by reference) including, for example, N-ethyl-ρ-menthane-3-carboxamide.

Suitable skin-soothing agents which can be utilized in the cyclodextrin inclusion complex include menthol, camphor, eugenol, eucalyptol, safrol, methyl salicylate, and the aforedescribed menthol analogs. Any suitable cyclodextrin may be utilized to form the inclusion complex including alphacyclodextrin, beta-cyclodextrin, gamma-cyclodextrin and modified cyclodextrins such as hydroxypropyl-beta-cyclodextrin, methyl-beta-cyclodextrin, and acetyl-betacyclodextrin. The preferred cyclodextrins are betacyclodextrin and gamma-cyclodextrin.

When the matrix material comprises a cyclodextrin inclusion complex, the matrix material may also advantageously comprise up to about 10%, preferably about 2% to about 7%, by weight of a displacing agent which displaces the skin-soothing agent from the inclusion complex upon contact with water, thereby enhancing the release of the skin-soothing agent from the skin engaging shaving aid member material during use. The displacing agent is a material which is capable of forming a more stable complex with the cyclodextrin than the complex formed with the skin soothing agent and, thus, displaces the skin-soothing agent from the complex when the skin engaging shaving aid member is contacted with water. Suitable displacing agents include surfactants, benzoic acids, and certain amines (e.g. urea). Further details with respect to the aforementioned cooling agents, cyclodextrin inclusion complexes and displacing agents may be found in U.S. Pat. Nos. 5,653,971, and, 5,713,131.

Those of skill in the art will understand that one or more of the cooling agents listed in this section as Optional Cooling Agents can also be used as the cooling agent in a form encapsulated within either the nano-particle and/or the micro-particle. The matrix material can further comprise one or more other skin care actives in a neat form. Non-limiting examples of suitable other skin care actives include those disclosed throughout this specification.

III. Encapsulated Actives

In some embodiments, the skin engaging shaving aid member of the present invention further comprises at least one encapsulated active. The encapsulated active can be, for example, a thermally resilient sensate, an additional sensate, a perfume or another skin care active or composition. In some embodiments, the level of said at least one encapsulated active (including the weight of the capsule and encapsulated active) is from about 0.01% to about 50% by weight of said skin engaging shaving aid member, alternatively from about 10% to about 45%, alternatively from about 15% to about 35%. The encapsulated actives can contain the same ingredients or different ingredients. The encapsulated actives can also include mixtures of ingredients.

Nonlimiting examples of encapsulation technology can be the nano and micro particles described in U.S. Pat. No. 7,115,282. The nano-particles of the present invention are hydrophobic in nature. In some embodiments, the nano-particles have an average diameter in the range from about 0.01 micron to about 10 microns, or from about 0.05 microns to about 5 microns, or from about 0.1 microns to about 2 microns. This linear dimension for any individual particle represents the length of the longest straight line joining two points on the surface of the particle. In some embodiments, a portion of the nano-particles are encapsulated into one or more water-sensitive micro-particles. In some embodiments, the majority of the nano-particles present in the skin engaging shaving aid member are encapsulated into said water-sensitive micro-particles. The micro-particles have an average particle size of from about 2.0 microns to about 100 microns, or from about 20 microns to about 100 microns.

The sensates of the present invention can be included as a neat ingredient (as a direct addition into the composition), in an encapsulate, or as a coating or separate layer. In some embodiments, one or more of the thermally resilient sensates can be present in both a neat form and in an encapsulate. In some embodiments, one of the thermally resilient sensates can be in a neat form and another sensate or thermally resilient sensate can be in an encapsulate. Further, in another embodiment, an additional sensate or an optional cooling agent (such as disclosed herein) can be present in a neat form along with one or both of the thermally resilient sensates of the present invention. For example, any of the above thermally resilient sensates can be used along with L-menthol, menthyl lacrate, or any other commonly used cooling agent, all as neat product, or with one or more cooling agents or sensates in the capsule.

In some embodiments the level of active or actives in the encapsulated active ranges from about 20% to about 90%, preferably from about 30% to about 75% by weight of the nano-particles. In some embodiments the level of the active or actives in the encapsulated active ranges from about 10% to about 60%, or from about 30% to about 50% by weight of the micro-particles. Lower levels of the encapsulated active can also be used, e.g. as low as 10%, or as low as 5%, or as low as 1%.

In some embodiments, encapsulated active comprises more than one cooling agent, for example L-menthol+Menthyl lactate (Frescolat ML); L-menthol+Menthone Glycerine Acetal (Frescolat MGA); or L-menthol+Coolact 10, or peppermint oil. In yet another embodiment, the encapsulated active comprises at least one cooling agent and a fragrance, a mineral oil, or a combination thereof. In another embodiment, the cooling agent comprises a mixture of menthol and menthyl lactate, such as described in WO 2007115593 (commercially available as Fresocolat Plus), or the eutectic mixture of menthol and menthyl lactate in a ratio of weight in the range of 1:4 to 4:1, as described in U.S. Pat. No. 6,897,195.

IV. Additional Skin Care Active Ingredients

Various skin care actives ("actives") which are commonly used for topical application can be included in the skin engaging shaving aid member as a neat product and/or in an encapsulate.

Non-limiting examples of suitable cooling agents include: L-menthol; p-menthane-3,8-diol; Isopulegol; Menthoxypropane-1,2-diol; Curcumin; Menthyl Lactate (such as Frescolat ML by Symrise); Gingerol; Icilin; Tea Tree Oil; Methyl Salicylate; Camphor; Peppermint Oil; N-Ethyl-ρ-menthane-3-carboxamide; Ethyl 3-(p-menthane-3-carboxamido)acetate; 2-Isopropyl-N,2,3-trimethylbutyramide; Menthone glycerol ketal, Menthone Glyerine Acetal; Coolact 10; and mixtures thereof. These and other cooling agents are known and described in various publications, such as U.S. Patent No. 2008/0300314A1, U.S. Pat. Nos. 5,451,404 and 7,482,373. In yet another embodiment, the cooling agent comprises one or more of the cooling agents previously described for use in various shave aids. See e.g., U.S. Pat. Nos. 5,095,619; 5,713,131; 5,095,619; 5,653,971; 6,298,558; 6,944,952; and 6,295,733.

Other actives suitable for cosmetic and dermatological use can be used herein. Non-limiting examples of suitable actives include one or more of: Bis-abolol and ginger extract, a surfactant derived from olive oil such as Olivem 450® and Olivem 460®, Lauryl p-Cresol Ketoxime, 4-(1-Phenylethyl)1,3-benzenediol, Lupin (*Lupinus albus*) oil & wheat (*Triticum vulgare*) germ oil unsaponifiables, Hydrolyzed lupin protein, Extract of L-lysine and L-arginine peptides, Oil soluble vitamin C, Evodia rutaecarpa fruit extract, Zinc pidolate and zinc PCA, Alpha-linoleic acid, p-thymol, and combinations thereof; at least one additional skin and/or hair care active selected from the group consisting of sugar amines, vitamin $B_3$, retinoids, hydroquinone, peptides, farnesol, phytosterol, dialkanoyl hydroxyproline, hexamidine, salicylic acid, N-acyl amino acid compounds, sunscreen actives, water soluble vitamins, oil soluble vitamins, hesperedin, mustard seed extract, glycyrrhizic acid, glycyrrhetinic acid, carnosine, Butylated Hydroxytoluene (BHT) and Butylated Hydroxyanisole (BHA), menthyl anthranilate, cetyl pyridinium chloride, tetrahydrocurmin, vanillin or its derivatives, ergothioneine, melanostatine, sterol esters, idebenone, dehydroacetic acid, Licohalcone A, creatine, creatinine, feverfew extract, yeast extract (e.g., Pitera®), beta glucans, alpha glucans, diethylhexyl syringylidene malonate, erythritol, p-cymen-7-ol, benzyl phenylacetate, 4-(4-methoxyphenyl)butan-2-one, ethoxyquin, tannic acid, gallic acid, octadecenedioic acid, p-cymen-5-ol, methyl sulfonyl methane, an avenathramide compound, fatty acids (especially poly-unsaturated fatty acids), antifungal agents, thiol compounds (e.g., N-acetyl cysteine, glutathione, thioglycolate), other vitamins (vitamin B 12), beta-carotene, ubiquinone, amino acids, their salts, their derivatives, their precursors, and/or combinations thereof; and a dermatologically acceptable carrier. These and other potentially suitable actives are described in greater detail in U.S. Patent Publication No. 2008/0069784.

Additional actives that can be used include those commercially available under the following tradenames: Signaline S, Jojoba Oil, Ceramidone, Net DG, Pal-GHK (Paltenex), Rhodysterol, Vital ET, and combinations thereof.

In another embodiment, the active can be a methyl naphthalenyl ketone. The methyl naphthalenyl ketone can be a 1-(1,2,3,4,5,6,7,8-octahydro-2,3,8,8-tetramethyl-2naphthalenyl)-ethan-1-one molecule or an isomer or derivative thereof. Commercially available as Iso-E-Super from IFF of New York. Other sensates can also be used, including those which have ability to up-regulate the TRPM8 receptor, which has been described as the cool menthol receptor. Non-limiting examples of suitable TRPM8 regulators include: p-menthane-3,8-diol; Isopulegol; Menthoxypropane-1,2-diol; Curcumin; Menthyl Lactate; Gingerol; Icilin; Menthol; Tea Tree Oil; Methyl Salicylate; Camphor; Peppermint Oil; N-Ethyl-p-menthane-3-carboxamide; Ethyl 3-(p-menthane-3-carboxamido)acetate; 2-Isopropyl-N,2,3-trimethylbutyramide; Menthone glycerol ketal, and mixtures thereof.

The active ingredient can also be one or more skin care actives suitable for topical use. The CTFA *Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, camphor, eucalyptus oil, eugenol, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, fatty alcohols and fatty acids, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents, skin-conditioning agents, skin soothing and/or healing agents and derivatives, skin treating agents, thickeners, and vitamins and derivatives thereof. Additional non-limiting examples of additional suitable skin treatment actives are included in U.S. 2003/0082219 in Section I (i.e. hexamidine, zinc oxide, and niacinamide); U.S. Pat. No. 5,665,339 at Section D (i.e. coolants, skin conditioning agents, sunscreens and pigments, and medicaments); and US 2005/0019356 (i.e. desquamation actives, anti-acne actives, chelators, flavonoids, and antimicrobial and antifungal actives). It should be noted, however, that many materials may provide more than one benefit, or operate via more than one mode of action. Therefore, classifications herein are made for the sake of convenience and are not intended to limit the active to that particular application or applications listed.

V. Shaving Head

According to some embodiments of the invention, a shaving device is provided, which generally comprises a shaving head and a handle or grip portion, upon which the shaving head is mounted. The shaving device can be manual or power driven and can be used for wet and/or dry application. The shaving head can be a razor cartridge where the device is a shaving razor. The shaving head may be replaceable and/or pivotally connected to a cartridge connecting structure and in turn or independently (e.g. permanently fixed) to a handle. In an some embodiments, the cartridge connecting structure includes at least one arm to releasably engage the shaving head.

The shaving head comprises one or more elongated edges (blades) usually positioned between a first and second end, said one or more elongated edges comprising a tip extending towards said first end. For example, U.S. Pat. No. 7,168,173 generally describes a Fusion® razor that is commercially available from The Gillette Company and which includes a razor cartridge with multiple blades. Additionally, the razor cartridge may include a guard as well as a skin engaging shaving aid member. A variety of razor cartridges can be used in accordance with the present invention. Nonlimiting examples of suitable razor cartridges, with and without fins, guards, and/or shave aids, include those marketed by The Gillette Company under the Fusion®, Venus® product lines as well as those disclosed in U.S. Pat. Nos. 7,197,825, 6,449,849, 6,442,839, 6,301,785, 6,298,558; 6,161,288, and U.S. Patent Publ. 2008/060201. Those of skill in the art will understand that the present skin engaging shaving aid member can be used with any currently marketed system or disposable razor, including those having 2, 3, 4 or 5 blades.

In some embodiments, said at least one skin engaging shaving aid member is located on the portion of the cartridge that contacts skin during the shaving process, forward and/or aft of the blades. A feature "forward" of the one or more elongated edges, for example, is positioned so that the surface to be treated with by the shaving device encounters the feature before it encounters the elongated edges. A feature "aft" of the elongated edge is positioned so that the surface to be treated by the shaving device encounters the feature after it encounters the elongated edges. Where more than one skin engaging shaving aid member is provided on the shaving device, they can be the same (identical) or different, in terms of physical shape/structure and/or chemical composition, and one or more of them may comprise the sensate.

In some embodiments, the cartridge comprises a guard comprising at least one elongated flexible protrusion to engage a user's skin. The at least one flexible protrusion may comprise flexible fins generally parallel to said one or more elongated edges. Said at least one flexible protrusion may additionally or alternatively comprise flexible fins comprising at least one portion which is not generally parallel to said one or more elongated edges. Non-limiting examples of suitable guards include those used in current razor blades and include those disclosed in U.S. Pat. Nos. 7,607,230 and 7,024,776; (disclosing elastomeric/flexible fin bars); 2008/0034590 (disclosing curved guard fins); 2009/0049695A1 (disclosing an elastomeric guard having guard forming at least one passage extending between an upper surface and a lower surface). In some embodiments, said skin engaging shaving aid member is positioned on the cartridge aft of the guard and forward of said elongated edge. In another embodiment, the skin engaging shaving aid member is positioned on the cartridge forward of the guard. This embodiment can be particularly useful to deliver the skin engaging shaving aid member prior to contact with the guard.

VI. Method of Making

Skin engaging shaving aid member of the present invention may be fabricated by any appropriate method, including injection molding, pressing, impregnation, spray-coating, calendaring and extrusion, or combinations of such steps. All of the components of the strip, including the thermally resilient sensates can be blended prior to molding or extrusion. For best results, it is preferred that the components are dry.

The blended components may be extruded through a Haake System 90, ¾ inch diameter extruder with a barrel pressure of about 1000-2000 psi, a rotor speed of about 10 to 50 rpm, and a temperature of about 150°-185° C. and a die temperature of about 170°-185° C. Alternatively, a 1¼ inch single screw extruder may be employed with a processing temperature of 175°-200° C., preferably 185°-190° C., a screw speed of 20 to 50 rpm, preferably 25 to 35 rpm, and an extrusion pressure of 1800 to 5000 psi, preferably 2000 to 3500 psi. The extruded strip is air cooled to about 25° C. To injection mold the strips it is preferred to first extrude the powder blend into pellets. This can be done on a 1¼ or 1½ inch single screw extruder at a temperature of 120°-180° C., preferably 140°-150° C., with a screw speed of 20 to 100 rpm, preferably 45 to 70 rpm. The pellets are then molded in either a single material molding or multi-material molding machine, which may be single cavity or multi-cavity, optionally equipped with a hot-runner system. The process temperature can be from 165° to 250° C., preferably from 180° to 225° C. The injection pressure should be sufficient to fill the part completely without flashing. Depending on the cavity size, configuration and quantity, the injection pressure can range from 300 to 2500 psi. The cycle time is dependent on the same parameters and can range from 3 to 30 seconds, with the optimum generally being about 6 to 15 seconds.

VII. Details on Figures

Figure 2:
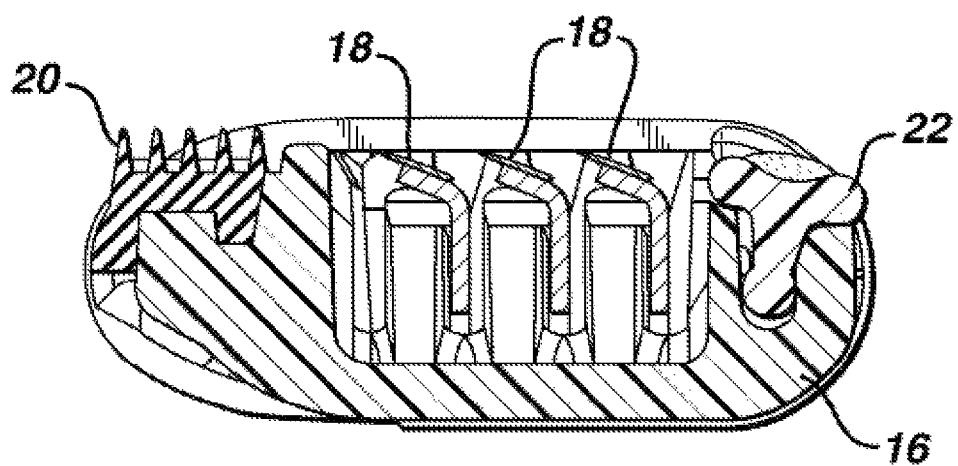
FIG. 2 is a sectional view taken along line 2-2 of FIG. 1.
Figure 3:
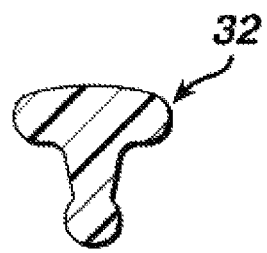
FIG. 3 is a side elevation view of a second type of skin engaging shaving aid member of the present invention.

Referring to FIGS. 1 and 2, the razor cartridge 14 includes housing 16, which carries three blades 18, a finned elastomeric guard 20, and a skin engaging shaving aid member 22 located on a skin-engaging portion (in this case the cap) of the cartridge. Skin engaging shaving aid member 22 is shown having two layers, the first layer can be the matrix and encapsulated active of the present invention, and the second layer can be a conventional shave aid, or vice versa. The skin engaging shaving aid member is preferably locked in (via adhesive, a fitment, or melt bonding) an opening in the rear of the cartridge. Skin engaging shaving aid member 32, shown in FIG. 3, is similar to skin engaging shaving aid member 22, except that skin engaging shaving aid member 32 has a homogeneous composition throughout and a uniform, slightly curved to flat upper surface. This type of skin engaging shaving aid member may also be fabricated in a wedge-shaped cross-section or any other desired shape. The skin engaging shaving aid member may also be constructed in two or more layers, such as a sandwich or a sheath/core construction.

The present invention may also include a method of use of a skin engaging shaving aid member to provide a cooling, tingling, refreshing, or otherwise topically noticeable sensation or feeling to a user by applying a skin engaging shaving aid member in accordance with at least one embodiment of the present invention onto a users' skin. This can be done as part of a process or method of shaving.

VIII. Examples

Examples 1-4 can be made according to the below table with the following method: ingredients are blended and mixed with other ingredients in a tumbler to make a homogeneous powder. The obtained powder is then single extruded into lubrastrips at 160-180° C. and 100-200 bar pressure.

| Ingredients | Example 1 wt % | Example 2 wt % | Example 3 wt % | Example 4 wt % |
| --- | --- | --- | --- | --- |
| Dow Polyox Coagulant (PEO) | 39.73 | 25.79 | 39.73 | 20.66 |
| Dow Polyox N-750 w/4% Vitamin E | 26.44 | 17.16 | 26.44 | 2.50 |
| Polystyrene 731G HIPS with Acrowax | 15.15 | 9.84 | 0.00 | 39.01 |
| ECM High Impact Polystyrene Pulverised 5410 | 0.00 | 0.00 | 15.15 | 19.15 |
| Dow Carbowax 4600PEG | 4.75 | 3.08 | 4.75 | 4.75 |
| Dow Tone Polymer P-767 | 4.70 | 3.05 | 0.00 | 0.00 |
| Solvay PCL Tone Polymer Capa 6506S | 0.00 | 0.00 | 4.70 | 4.70 |
| Ciba-Geigy B215 Irganox Antioxidant | 0.24 | 0.15 | 0.24 | 0.24 |
| Aloe | 0.19 | 0.12 | 0.19 | 0.19 |
| Colorant | 3.80 | 2.47 | 3.8 | 3.80 |
| Salvona MultiSal 160 L-Menthol (30% menthol load) | 0.00 | 33.33 | 0.00 | 0.00 |
| Givaudan G180 Coolant (n-para-benzene acetonitrile menthane carboxamide) | 5.00 | 5.00 | 5.00 | 5.00 |

Example 3 was made and tested by ten male shavers who shave at least four times per week and who are cooling sensitive, meaning they were pre-screened by shaving a razor product with cooling lubrastrip against a razor product with non-cooling lubrastrip, using a split face protocol and indicating that they could perceive the cooling sensation and thus discriminate the two razor products. Each person has shaved three razor products with lubrastrip as the only variant. A can of Gillette Series Sensitive Skin Shave Gel was used for each shave to minimize the shave prep variation effect on cooling sensitivity detection. The shaving context for each person was kept as close as possible through the entire shave test, for example the only variation between razors was the lubrastrip and the same shaving preparation (Gillette Series Sensitive Skin Shave Gel) was used for every experiment. The shaving order of products was randomized in order to cancel possible product interference. Each razor product was used for five normal shaves. The ten shavers scored their perceived cooling during and after shaving on a scale from 0 to 10 (where 0 indicates no cooling sensation perceived). These scores were averaged and the results appear in the table below:

|  | Example 3 |
| --- | --- |
| Cooling Intensity during shaving | 2.72 |
| Cooling intensity after shaving | 4.12 |

The results show that the coolants are able to withstand the extrusion process and provide shaver-noticeable cooling benefit both during and after shaving. Importantly, with these test subjects, the cooling intensity was shown to increase after shaving compared to during shaving. This was surprising and unexpected as the additional of many other coolants in general into such shaving aids was not originally considered to be able to provide meaningful noticeable impacts on many users.

The following comparative example, containing 5% menthol, was also produced using the method above, and tested by four male shavers who shave at least four times per week and who are cooling sensitive as above. The shavers reported they were unable to detect any cooling effect.

| Ingredients | Comparative Example 1 wt % |
| --- | --- |
| Dow Polyox Coagulant (PEO) | 34.85 |
| Dow Polyox N-750 w/4% Vitamin E | 23.19 |
| Polystyrene Nova 5410 HIPS | 13.29 |
| Dow Carbowax 4600PEG | 4.17 |
| Solvay PCL Tone Polymer Capa 6506S | 4.13 |
| Ciba-Geigy B215 Irganox Antioxidant | 0.21 |
| Aloe | 0.17 |
| Colorant | 3.33 |
| Salvona MultiSal 160 L-Menthol (30% menthol load) | 16.66 |

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein. Similarly, it should be understood that each feature of the each specified embodiment of the invention may be independently applied to each other specified embodiment, as if all such combinations were expressly written herein, unless these combinations are specifically excluded or the relevant features are innately incompatible (e.g. the features are directly contradictory).

All parts, ratios, and percentages herein, in the Description, Examples, and Claims, are by weight of the shaving aid member and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the DETAILED DESCRIPTION OF THE INVENTION are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern. Except as otherwise noted, the articles "a," "an," and "the" mean "one or more."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin engaging shaving aid member, said skin engaging shaving aid member comprising:
   a. a matrix comprising at least one of: a water soluble polymer, an emollient, and a soap base, wherein the water soluble polymer is at a level of from about 50% to about 100%, by weight of the matrix;
   b. from about 5% to about 15%, by weight of the skin engaging shaving aid member, of a thermally resilient sensate, the thermally resilient sensate comprising N-[4-(cyanomethyl)phenyl]-(1R,2S,5R)-2-isopropyl-5-methylcyclohexanecarboxamide of formula:

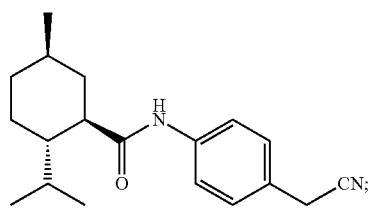 [SMILES: CC(C)[C@@H]1CC[C@@H](C)C[C@H]1C(=O)Nc1ccc(CC#N)cc1]

and
   c. from about 15% to about 35%, by weight of the skin engaging shaving aid member, of a water insoluble polymer.

2. The skin engaging shaving aid member of claim 1, further comprising an optional cooling agent selected from the group consisting of: L-menthol; p-menthane-3,8-diol; Isopulegol; Menthoxypropane-1,2,-diol; Curcumin; Menthyl Lactate; Gingerol; Icilin; Tea Tree Oil; Methyl Salicylate; Camphor; Peppermint Oil; N-Ethyl-p-menthane-3-carboxamide; Ethyl 3-(p-menthane-3-carboxamido)acetate; 2-Isopropyl-N,2,3-trimethylbutyramide; Menthone glycerol ketal, Menthone Glyerine Acetal; and mixtures thereof.

3. The skin engaging shaving aid member of claim 2, wherein said optional cooling agent is a mixture of L-menthol and menthyl lactate in a ratio of weight in the range of 1:4 to 4:1.

4. The skin engaging shaving aid member of claim 1, further comprising an encapsulated active present at a level of from about 0.01% to about 50% by weight of the skin engaging shaving aid member.

5. The skin engaging shaving aid member of claim 1, wherein the water soluble polymer comprises at least one of: a polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, and silicone polymer.

6. The skin engaging shaving aid member of claim 1, wherein said water insoluble polymer comprises at least one of: polyethylene, polypropylene, polystyrene, high impact polystyrene, butadiene styrene copolymer, polyacetal, acrylonitrile-butadiene styrene copolymer, and ethylene vinyl acetate copolymer.

7. The skin engaging shaving aid member of claim 1, wherein said matrix further comprises a block polymer selected from the group consisting of: a di-block copolymer, a tri-block copolymer, a multi-block copolymer, a radial block copolymer, a random block copolymer, and mixtures thereof.

8. The skin engaging member of claim 1, wherein said water soluble polymer comprises polyethylene oxide.

9. A shaving device comprising:
   a. a cartridge;
   b. one or more elongated edges positioned on said cartridge; and
   c. the skin engaging shaving aid member of claim 1 positioned on said cartridge.

* * * * *